United States Patent [19]
Pilgrim

[11] 4,152,078
[45] May 1, 1979

[54] GRANULATING APPARATUS

[75] Inventor: Thomas A. Pilgrim, Edwalton, England

[73] Assignee: BPB Industries Limited, United Kingdom

[21] Appl. No.: 703,999

[22] Filed: Jul. 9, 1976

Related U.S. Application Data

[63] Continuation of Ser. No. 614,409, Sep. 18, 1975, abandoned, which is a continuation of Ser. No. 438,339, Jan. 31, 1974, Pat. No. 3,950,181.

[30] Foreign Application Priority Data

Feb. 1, 1973 [GB] United Kingdom ............... 5144/73
Jan. 7, 1974 [GB] United Kingdom ................ 589/74

[51] Int. Cl.² .......................... B01F 15/06; B01F 9/22
[52] U.S. Cl. .................................. 366/144; 366/162; 366/219; 366/287
[58] Field of Search ............................ 259/2, 11-12, 259/28-29, 35, 72, 93, 174; 366/144, 160, 219, 287, 288, 162

[56] References Cited

U.S. PATENT DOCUMENTS

| 2,000,645 | 5/1935 | Rector | 259/93 |
| 2,125,046 | 7/1938 | Crandell | 259/2 |
| 3,693,942 | 9/1972 | Foucault | 259/2 |

Primary Examiner—Robert W. Jenkins
Attorney, Agent, or Firm—Kenneth E. Roberts; Robert H. Robinson; Samuel Kurlandsky

[57] ABSTRACT

Porous gypsum granules are produced by adding powdered plaster to a stable aqueous foam and agitating the foam until granules of desired size are formed. Agitation is terminated before the foam collapses, but when the foam has subsequently collapsed the damp granules are recovered and dried. The product granules have a generally spheroidal shape mainly in the size range 0.25 to 2 mm, with a fine compact outer surface layer and a coarser interior with voids which confer high absorbency. These can be used as carriers for active materials such as herbicides or insecticides for agricultural or horticultural purposes or as fillers for plastics. Apparatus for continuously mixing fluid materials and suitable for use with foam and gypsum consists of a trough-shaped conveyor with a series of rotary agitators spaced along it.

4 Claims, 9 Drawing Figures

X30

X950

X 4750

X 4750

GRANULATING APPARATUS

This is a continuation, of application Ser. No. 614,409, filed Sept. 18, 1975, now abandoned, which is a continuation of application 438,339, filed Jan. 31, 1974, now U.S. Pat. No. 3,950,181.

The present invention relates to appearance for mixing materials while undergoing a physical or chemical change, and more especially for the preparation of gypsum (calcium sulphate dihydrate) in the form of porous, lightweight granules. granules of also relates to an improved method of preparing porous granules of gypsum.

Gypsum may conventionally be produced in pelleted form by tumbling the powdered gypsum. The mineral or plaster in a rotating drum or pelletizer and adding sufficient liquid, usually water, to cause the powder to agglomerate into larger aggregates. The rolling action imparted to these aggregates by the rotating drum or pan causes the agglomerates to assume a spheroidal shape. The equipment is arranged to discharge the pellets when they have reached a chosen size: the discharged pellets are subsequently dried and suitably packed. Pellets produced by the conventional means are generally dense.

The present invention now provides a method of preparing porous gypsum granules in which powdered gypsum plaster in suspension in a stable aqueous foam is agitated until granules of desired size are formed in suspension in the foam, agitation being terminated before the foam collapses, and thereafter when the plaster has set the foam is caused or allowed to collapse and the resulting discrete porous granules are dried. It appears that certain fractions of the plaster hydrate before the rest and produce nuclei around which gypsum granules form. By a "stable" aqueous foam is mount a foam which has sufficient strength or stability to support the added plaster powder without collapsing.

Although gypsum granules can be produced by a batch process, as described below, there are practical disadvantages in batch processing which make a continuous process preferable. Among the principal disadvantages is the limitation on batch quantities which arises because the rapid addition of a large quantity of plaster powder to a body of foam in a mixing vessel tends to cause premature collapse of the foam. Also, it is more difficult in batch processing to control the size of the granules or to achieve consistent batches.

According to the preferred practice of the invention, stable foam is produced from water and a foaming agent and formed into a continuously advancing bed, and powdered hemihydrate plaster is metered continuously on top of the advancing bed of foam and stirred in. Thereafter agitation is continued and granules are formed in suspension in the foam as the plaster progressively hydrates. Mixing can be continued, if desired, up to the point where the foam is about to collapse but should not be further prolonged, since a higher density slurry would then result. The plaster granules may not be fully hydrated at the end of mixing but they should be sufficiently structured or set to retain their generally spherical shape and discrete identity after the collapse of the foam. Excess water, if any, is removed and the granules dried, for example by conventional driers such as revolving heated tube, a drying tunnel or in a fluidised bed.

In an alternative batch method, an aqueous foam is produced in a suitable vessel equipped with a rotating agitator. A predetermined quantity of hemihydrate plaster is sprinkled onto the continuously agitated foam and mixed until granules are formed or until the foam is about to collapse. On completion of this mixing, the contents of the vessel are poured onto a suitable surface and left for the foam to collapse. Spheroidal granules remain and are dried in a suitable oven or other conventional drying means.

The granules obtained in accordance with this invention are porous and generally spheroidal, with hard, rounded surfaces. They usually have diameter within the range 0.25 to 2.0 mm. They may be used as carriers of chemicals (with which they may be impregnated), such as biologically or agriculturally active compounds, as a non-dusting composition or soil conditioner for application to agricultural or horticultural land, as a gypsum aggregate for incorporation in the manufacture of plasters and cements, or as a non-combustible filler in plastics.

For most end uses of the granules there are specific ranges of sizes that are most satisfactory. The size of the spheroidal granules appears to depend mainly on five factors, and control fo these enables the granule size to be controlled. These factors are: the particle size of the plaster - finer particles tend to make finer granules; the dispersibility of the plaster in water, i.e. the magnitude of the specific surface which is rapidly attained - a more dispersible plaster tends to make finer granules; the period of agitation; the plaster:water ratio - for a given plaster an increase in the amount of water produces larger proportions of coarser granules; and the cell size within the initial aqueous foam - cell size depends to some extent on the nature of the foaming agent. For a given plaster perhaps the most important and readily variable factor is the period of agitation or mixing. For a continuous mixing system of given dimensions, the mixing period can be adjusted by varying the throughput within limits set, on the one hand, by loss of strength of the product if the throughput is too fast and, on the other hand, by collapse of the foam with agglomeration of the damp granules, if the throughput is too slow.

It is important that a stable foam be formed before addition of the plaster powder. Coarse, weak foams tend to collapse earlier and give weaker granules. The foam can be produced by agitation of a solution of a foaming agent in air. The nature and concentration of the foaming agent is not critical provided a stable foam is produced. Sodium alkylbenzene sulphonates are satisfactory but the agents at present preferred are alkali metal salts of sulphated fatty alcohol polyglycol ethers. Preferred concentrations of foaming agent lie within the range 0.2 to 2% by weight of water.

A wide range of hemihydrate plasters has been found to give satisfactory granules by the process of this invention. Common additives such as accelerators can be employed, although where a continuous process is operated, set gypsum adhering to the mixing section of the plant may suffice to give an accelerating action. The pH of the granules may be adjusted, for example by adding an acidulant. Whether such an addition is required will depend on the composition of the gypsum source from which the plaster employed was made, and upon the particular pH requirements for the intended end use of the granules.

For a given plaster, an increase in the ratio of water to plaster produces a greater proportion of coarser granules, although usually a predominance of granules within the size range 0.5 to 2.0 mm. Preferred weight ratios of water:plaster are 40–100:100 and in the case of the continuous method 30–100:100 depending on the granule size required and the water demand of the plaster. In the batch process it may be difficult to produce granules at the lower limit of water ratio because of a tendency to premature collapse of the foam.

The present invention further provides an apparatus suitable for the continuous production of porous or lightweight gypsum granules from a foamed aqueous slurry of gypsum plaster, or for other situations where a slurried material must be mixed while undergoing a change.

The apparatus is characterized by a trough along which the material to be mixed can be passed, and a series of agitators spaced along the trough and disposed to agitate continuously material being passed along the trough. Where the apparatus is to be used to prepare gypsum granules an upstream portion of the trough is associated with the necessary means for preparing and supplying to or for forming on the trough a foamed aqueous slurry of gypsum plaster, usually calcium sulphate hemihydrate, while a downstream portion of the trough is associated with means for drying and screening the gypsum granules formed by setting of the plaster.

The trough may be stationary, and the plaster-containing foam may be passed along it by pressure of succeeding plaster foam or by the action of the agitators. Alternatively, the trough may be constituted by a conveyor belt, or a portion of a conveyor belt, which can conveniently be constrained to form a trough, at least in the part occupied by the agitators, by being caused to pass through a rigid support trough, as of metal. Other suitable support means may, however, be adopted, for example a series of inclined supporting rollers or drums.

The trough may be straight or elongated or endless. In the first case the feed means will be at the upstream end and the drying means at the downstream end of the conveyor. In the second case the trough takes a closed, e.g. circular, path and the feed means and drying means are disposed at inlet and output stations spaced apart around the circuit of the trough.

The agitators may be of any construction that exerts an adequate mixing action over the whole width of the trough, without leaving dead zones in which setting plaster can accumulate. Suitable forms of agitator are rotary whisks or blades. There may have a diameter substantially equal to the width of the trough or may have a smaller diameter and be moved regularly across the trough, either with a reciprocating or with a planetary movement.

Preferred forms of the apparatus are shown in the accompanying drawings, in which.

Figure 6A:
FIG. 6 represents microphotographs of the granules produced.

FIG. 6A showing a number of such granules and 6B, 6C and 6D showing different portions of a cut granule at different magnifications.

Figure 1:
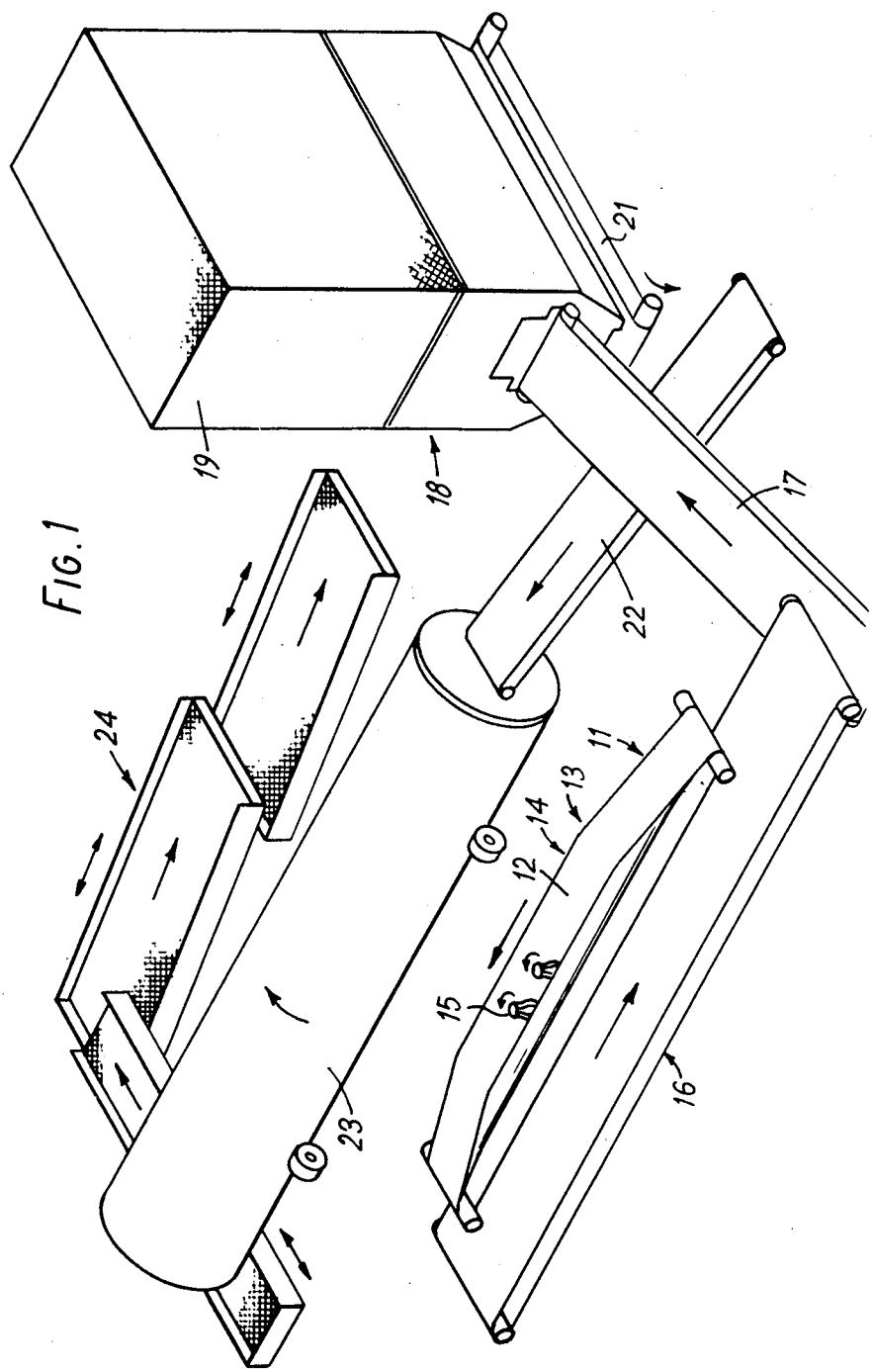
FIG. 1 is a diagrammatic view of apparatus according to this invention for the continuous production of gypsum granules and including a conveyor belt.

The apparatus shown in FIG. 1 includes a mixing conveyor 11, movable in the direction of the arrow, of which the upper run is constrained to form a trough section 12 by a metal support trough which, for the sake of clarity in the drawing, is not shown. A foaming device (not shown) for producing foam from water and a foaming agent is disposed to deliver a stable foam onto the conveyor at 13 and a solids dispenser (also not shown) is disposed to meter powdered plaster onto the conveyor at 14. Those devices may be conventional in character. A premixing unit may be placed before the first agitator as an homogeniser of foam and plaster and may take the form of equipment to evenly distribute dry plaster onto the bed of foam or equipment which intimately mixes the foam and plaster together.

Agitators 15, for example twelve in number, are disposed in the trough section 12 and a flat conveyor 16, on which material from the mixing conveyor 11 settles, extends beneath and beyond the mixing conveyor to deliver the material to an elevator 17 leading to a first stage drier 18.

Above the drier 18 is mounted a dust filter 19 to remove dust from exhaust hot air from the drier, and below the drier is a conveyor 21 arranged to deliver initially dried material to an elevator 22 for transfer to a second stage drier 23. The drier 23 is an inclined rotary drier and is arranged to deliver dried gypsum granules to a series of vibrating sieves 24 for classification.

Figure 2:
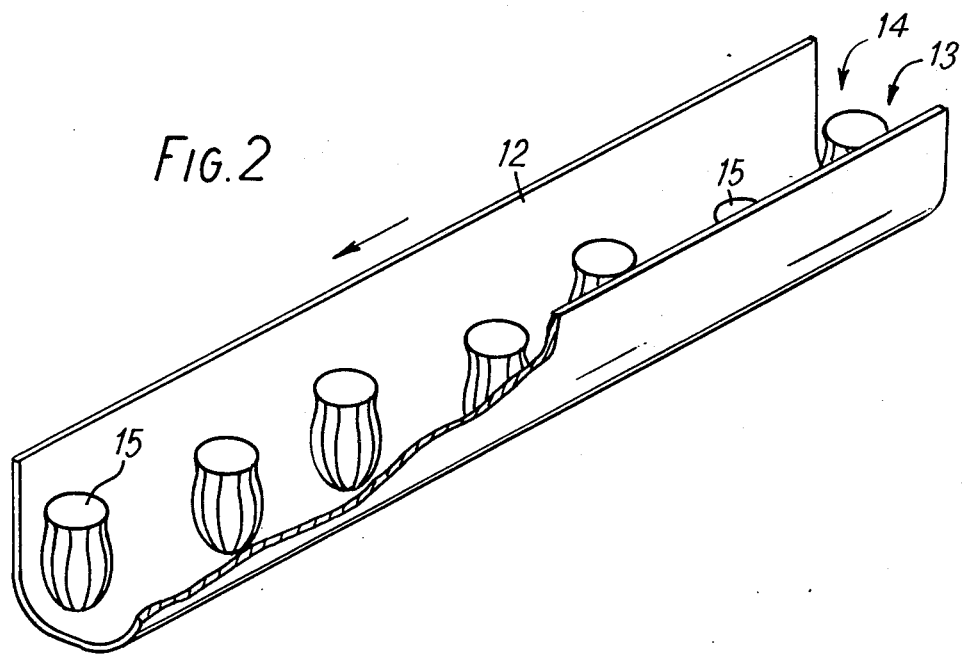
FIG. 2 is a fragmentary view of the conveyor belt and associated agitators as used in the apparatus of FIG. 1.
Figure 3:
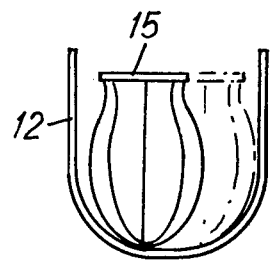
FIG. 3 and FIG. 4 are respectively a vertical cross section and top plan view of part of the trough showing the movement of agitators.
Figure 4:
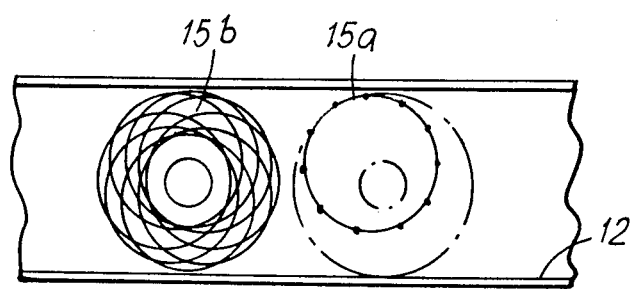

The trough 12 and agitators 15 are shown in greater detail in FIGS. 2 to 4. The agitators are mounted along the centre line of the trough and in this example are cage type whisks driven with a planetary motion as indicated by the arrows and the chain dotted representations. The position of one whisk 15a and the locus of movement of the neighbouring whisk 15b are shown in the plan view of FIG. 4.

The operation of the apparatus is as follows:

A foam consisting of water and foaming agent with a plaster accelerator if necessary is continuously fed onto the belt at the point 13 at the beginning of the trough 12 with hemihydrate plaster continuously metered in proportion at the point 14 on top of the foam. As the conveyor belt 11 proceeds along the trough the mix comes into the area of the first of the agitators 15 where the platter and foam are mixed together. As the conveyor proceeds so the mix is passed through the series of agitators placed inside the trough. The maximum length of time to pass through the mixing section is governed by the dimensions and speed of the conveyor and is established in dependence on the time necessary for setting or structuring of the plaster and the time required for the formation of granules of the desired size, and is limited to the period for which the foam matrix can be sustained.

By this means it is possible to ensure that the first unit volume of plaster which enters the first area of agitation will also be the first volume of plaster to leave the last agitator, substantially uncontaminated by preceding or following materials. Thus the second unit volume of plaster to pass through the first area of agitation is the second volume of plaster to leave the final agitator and so on. Metering is continuous and the mix is successively agitated for a period necessary to form the granules.

The set material, which is in the form of granules surrounded by and suspended in foam, then falls onto the settling conveyor 16 where the foam collapses leaving damp but mainly individual granules. The damp granules then fall onto the elevator 17 and pass successively through the driers 18 and 23 to be finally classified by the vibrating sieves 24.

It is possible using this same principle to obtain the same result from a differently shaped trough. For example, in the case previously described the trough is in a straight line with mixers placed progressively down its length, but the same effect may be obtained from a trough with ends joined to form a circle. In this case agitators are closely spaced within the trough, leaving a section clear where ingredients are fed in and mixed material is discharged.

Figure 5:
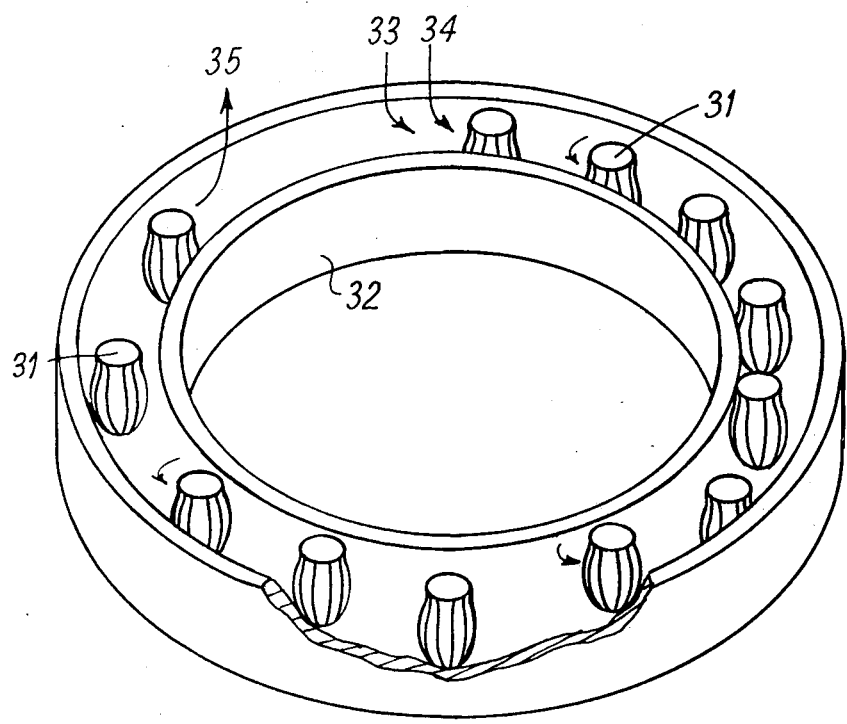
FIG. 5 is a diagrammatic view of an endless stationary trough and associated agitators.

An example of such an arrangement is shown in FIG. 5 where a series of agitators 31 is arranged round a slowly rotating troughed annular bowl 32. Aqueous foam and powdered gypsum plaster are introduced into the trough at the points 33 and 34 respectively, in the space between the last and the first agitator in the series, and the granular set material is drawn off from the trough at the point 35 after the last agitator.

The agitator 31 may be of the same planetary whisk type as those described with reference to FIGS. 3 and 4 in the case of the straight trough.

The principle so described can be used to produce varying outputs of mix, depending on the number of agitators, the length of the trough, the cross section of the trough and the speed of the mix passing through the total volume of agitation.

Apparatus constructed and functioning in accordance with this principle may also be used for materials other than plaster where ingredients are required to be mixed whilst a physical or chemical effect is taking place, and where it is prepared that each unit volume of material should not be influenced by materials which precede or follow.

The following are typical examples of the practice of this invention.

EXAMPLE 1

This example illustrated the production of porous grypsum granules by a batch process.

Aluminium sulphate (2.2 parts by weight), as plaster accelerator and acidulant, and sodium alkylbenzene sulphonate (0.3 part by weight) as foaming agent, are dissolved in water (37.5 parts by weight) and the solution agitated in air in a mixing vessel with a rotary whisk to form a foam. Hemihydrate plaster (60.0 parts by weight) is then sprinkled onto the foam and agitation continued.

On mixing of plaster aqueous foam, individual particles of plaster begin to hydrate or set, so that the foam becomes interspersed with spheres of gypsum. As mixing continues, the number of spheres per unit volume and the diameter of the spheres increase until, upon the occurrence of the main set temperature rises and the foam begins a rapid collapse. At this point agitation is stopped - further agitation beyond this point causes agglomeration of the spheres leading to a coagulated mass - and the contents of the mixing vessel are poured out and allowed to stand.

Within 15 minutes the foam completely collapses leaving damp but separate granules which are then dried with warm air or by other suitable means. The dried granules are found to have hard smooth surfaces and excellent flow properties, but are porous and have a good capacity for absorbing active materials such as herbicides or insecticides.

The sieve analysis of the product is as follows:

| Size (B.S. sieve) | Percentage | Dry Bulk Density (g/cc) |
| --- | --- | --- |
| + 10 | 2 | 0.71 |
| − 10 + 22 | 57 | 0.80 |
| − 22 + 36 | 29 | 0.75 |
| − 36 | 12 | 0.75 |

EXAMPLE 2

This example illustrates the production of porous gypsum granules by a continuous process.

In one typical example of the use of the apparatus described above, gypsum stucco having a specific surface of 6000 $cm^2/g$. and a foamed aqueous solution containing 0.5% by weight of a foaming agent comprising the sodium salt of a sulphated lauryl myristyl alcohol polyglycol ether ("Lutensit" - BASF) were supplied continuously in relative proportions (by weight) of 2:1. The wet bulk density of the mixture was 150 $Kg/m^3$.

The mixing conveyor had four agitation sections with speeds of agitation decreasing from 150 r.p.m. in the first stage to 80 r.p.m. in the last stage. The mean residence time in the agitation zone was 4 minutes and the foam collapsed 6 minutes after leaving the agitation zone, leaving discrete granules. The granules were then retained for 60 minutes on the settling conveyor and thereafter dried and screened. The following sieve analysis was established for the product:

| B.S. mesh | % by weight retained |
| --- | --- |
| + 10 | 4.23 |
| − 22 + 22 | 24.78 |
| − 22 + 44 | 60.70 |
| − 44 + 60 | 8.56 |
| − 60 + 100 | 1.68 |
| − 100 | 0.05 |
| | 100.00 |

The photographs in FIG. 6 show various aspects of the granules produced by this invention.

FIG. 6a is a view of a number of porous granules according to the invention, which shows their generally spheroidal shape.

Figure 6B:
Figure 6C:
Figure 6D:

FIG. 6b is a microphotograph of the edge of a cut granule where the cut section meets the surface of the granule. It will be seen that the surface of the granule, which appears in the lower left-hand portion of the Figure, is composed of relatively tightly packed, small crystals of gypsum, as shown at even greater magnification in FIG. 6c. The cut section, showing the interior of the granule, appears at the upper right-hand side of FIG. 6b and is composed of larger crystals of gypsum which are more widely spaced and which enclose numerous voids, as shown in greater magnification in FIG. 6d.

The invention thus further provides a porous gypsum granule having a generally spheroidal shape and an outer surface layer composed of gypsum crystals that are smaller and more closely packed than the crystals of the interior of the granule, the interior of the granule exhibiting irregular voids or regions of low density that contribute to the absorbent capacity of the granule.

This structure is of considerable value. The close hard surface ensures good resistance to mechanical damage in handling, storage and use, while the more open interior confers a high absorbency and good loading capacity for impregnants, rendering the granules most suitable as a granular carrier.

I claim:

1. Apparatus for continuous production of porous gypsum granules from gypsum plaster in suspension in a stable aqueous foam comprising a continuously moving trough along which the material to be mixed can be passed, means for continuously supplying a stable aqueous foam in an upstream portion of the trough, means for continuously metering powdered gypsum plaster in a portion of the trough downstream from the foam supplying means, a series of agitators spaced along the trough downstream from the plaster supply means and disposed to agitate continuously material being passed along the trough, each agitator having a planetary movement about an axis to cover in its movement the entire width of the trough, a discharge portion in the trough downstream from the agitators to receive the collapsing foam and formed gyspum granules, settling means for recovering gypsum granules from the residual foam, and means for drying the granules.

2. The apparatus of claim 1 in which the trough is disposed in a straight line path and comprises a continuously moving conveyor belt, and support means constraining at least a part of the belt to form a trough along which the material to be mixed can be passed.

3. The apparatus of claim 1 in which the trough takes a closed, circular path comprising a slowly moving rotating annular trough-shaped bowl; and the feed means and drying means are disposed at inlet and outlet stations respectively spaced apart around the circuit of the trough.

4. The apparatus of claim 1 in which the settling means comprises an endless moving conveyor belt where upon the foam collapses leaving damp granules to be passed onto the drying means.

* * * * *

UNITED STATES PATENT AND TRADEMARK OFFICE
CERTIFICATE OF CORRECTION

PATENT NO. : 4,152,078

DATED : May 1, 1979

INVENTOR(S) : Thomas A. Pilgrim, Edwalton, England

It is certified that error appears in the above-identified patent and that said Letters Patent are hereby corrected as shown below:

In column 1, line 12 "granules. granules of" should read -- granules. It --.

In column 1, line 16 "gypsum. The mineral" should read -- gypsum mineral --.

In column 1, line 37 "is mount" should read -- is meant --.

In column 2, line 13 "diameter within" should read -- diameters within --.

In column 2, line 25 "fo these" should read -- of these --.

In column 2, line 34 "foam - cell" should read -- foam - the cell --.

In column 4, line 13 "Those devices" should read -- These devices --.

In column 5, line 25 "The agitator 31" should read -- The agitators 31 --.

In column 5, line 37 "it is prepared" should read -- it is preferred --.

In column 5, line 44 "example illustrated" should read -- example illustrates --.

In column 5, line 45 "grypum granules" should read -- gypsum granules --.

In column 6, line 38 "-22+22" should read -10+22 --.

UNITED STATES PATENT AND TRADEMARK OFFICE
CERTIFICATE OF CORRECTION

PATENT NO. : 4,152,078
DATED : May 1, 1979
INVENTOR(S) : Thomas A. Pilgrim, Edwalton, England It is certified that error appears in the above-identified patent and that said Letters Patent are hereby corrected as shown below:

In claim 1 column 8, line 2, "gyspum granules" should read -- gypsum granules --.

Signed and Sealed this

Fourteenth Day of August 1979

[SEAL]

Attest:

Attesting Officer

LUTRELLE F. PARKER
Acting Commissioner of Patents and Trademarks